United States Patent
Kuo et al.

(10) Patent No.: US 9,359,373 B1
(45) Date of Patent: Jun. 7, 2016

(54) LIPOPHILIC N-SUBSTITUTED NORCANTHARIMIDE DERIVATIVES AND USES THEREOF

(71) Applicants: Taipei Veterans General Hospital, Taipei (TW); National Chiayi University, Chiayi (TW); Mackay Memorial Hospital, Taipei (TW)

(72) Inventors: Cheng-Deng Kuo, Taipei (TW); Yu-Jen Chen, Taipei (TW); Jin-Yi Wu, Chiayi (TW); Hui-Fen Liao, Chiayi (TW)

(73) Assignees: TAIPEI VETERANS GENERAL HOSPITAL, Taipei (TW); NATIONAL CHIAYI UNIVERSITY, Chiayi (TW); MACKAY MEMORIAL HOSPITAL, Taipei (TW)

( * ) Notice: Subject to any disclaimer, the term of this patent is extended or adjusted under 35 U.S.C. 154(b) by 0 days.

(21) Appl. No.: 14/550,490

(22) Filed: Nov. 21, 2014

(51) Int. Cl.
*C07D 491/18* (2006.01)

(52) U.S. Cl.
CPC .................................... *C07D 491/18* (2013.01)

(58) Field of Classification Search
CPC .................................................... C07D 491/18
USPC ......................................................... 548/430
See application file for complete search history.

(56) References Cited

U.S. PATENT DOCUMENTS

2010/0137294 A1\* 6/2010 Gasser ................... A01N 43/90
514/228.2

FOREIGN PATENT DOCUMENTS

WO  WO 2015073802 A1 \* 5/2015 ............. A61K 45/06

OTHER PUBLICATIONS

Wu, et al. Molecule (2014), 19(6), 6911-6928.\*
Campbell et al. Bioorganic & Medicinal Chemistry Letters (2011), 21(11), 3277-3281.\*
Hill et al. Bioorganic & Medicinal Chemistry (2007), 15(18), pp. 6126-6134.\*

\* cited by examiner

*Primary Examiner* — Nyeemah A Grazier
(74) *Attorney, Agent, or Firm* — Muncy, Geissler, Olds & Lowe, P.C.

(57) ABSTRACT

Novel N-substituted norcantharimide derivatives are disclosed herein. The novel N-substituted norcantharimide derivatives are useful as lead compounds for manufacturing a medicament or a pharmaceutical composition for treating cancer, particularly for treating leukemia.

12 Claims, 11 Drawing Sheets

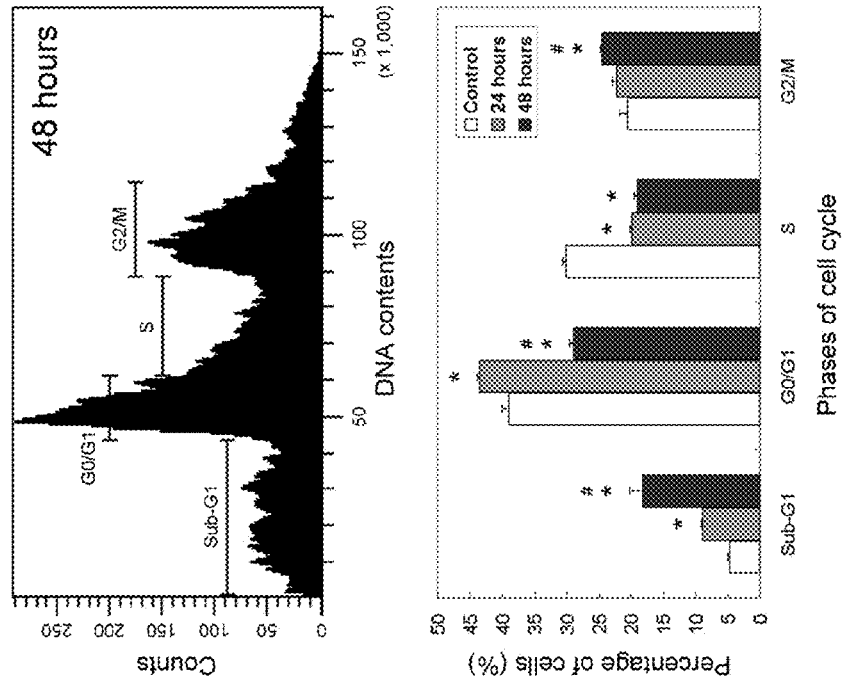
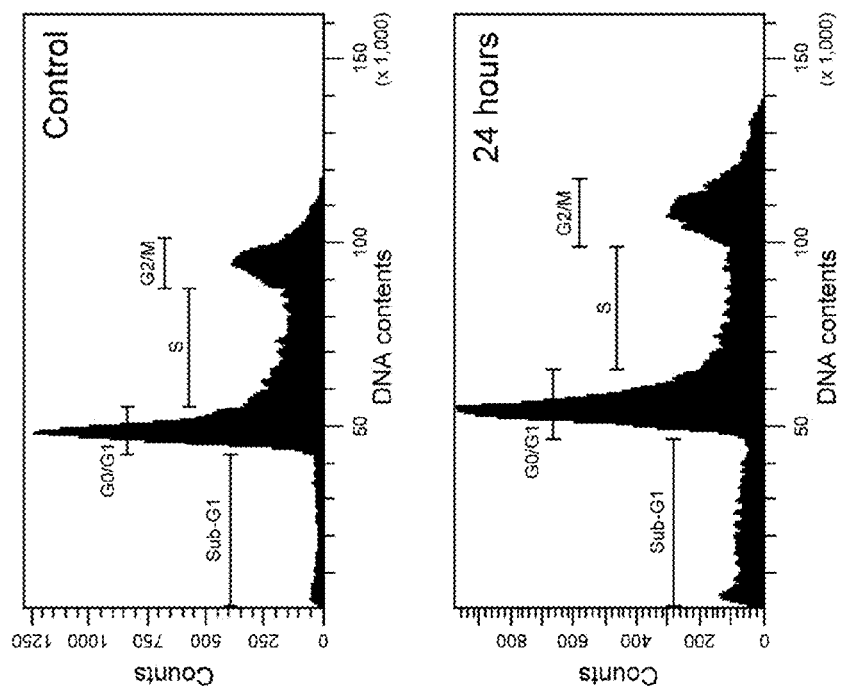

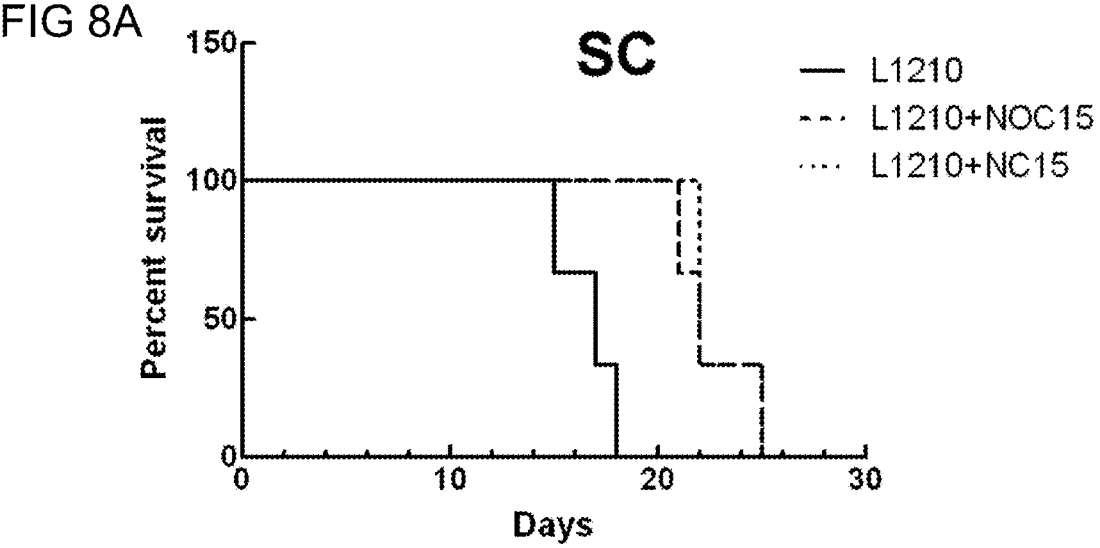
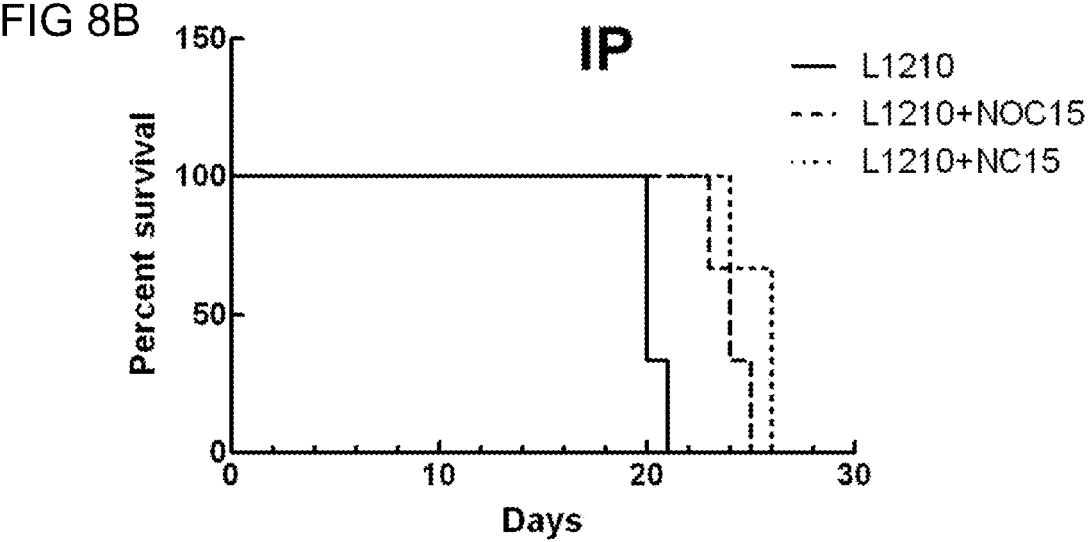

LIPOPHILIC N-SUBSTITUTED NORCANTHARIMIDE DERIVATIVES AND USES THEREOF

BACKGROUND OF THE INVENTION

1. Field of the Invention

The present disclosure relates to novel synthetic compounds of N-substituted norcantharimide derivatives, and their uses for manufacturing a medicament or a pharmaceutical composition for treating cancer.

2. Description of Related Art

Cantharidin, one of the active compounds isolated from Mylabris, is a potent serine/threonine protein phosphatase 1 (PP1) and phosphatase 2A (PP2A) inhibitor, and has been shown to possess anti-cancer properties both in vitro and in vivo. However, it was also found to be poisonous to the kidney and liver. Research in the past has tried to identify analogues and/or derivatives of cantharidin that exhibit anti-cancer activity without significant cytotoxicity towards normal tissues, and norcantharidin and norcantharimide have thus been produced. Norcantharidin, which is the de-methylated form of cantharidin, is found to possess less nephrotoxicity, yet the demethylation also results in a lower bioactivity. As to norcantharimide, its analogues bearing long alkyl chain at N-position have been suggested to possess enhanced bioactivity due to the improved uptake conferred by the hydrophorbic nature of the alkyl chain.

Accordingly, there exists in the related art a need of an analogue and/or a derivative of cantharidin that exhibits excellent selective cytotoxicity toward cancerous cells but not the normal cells.

SUMMARY

The present disclosure is based, at least in part, unexpected discovery that two N-substituted norcantharimide derivatives may retard the growth of cancerous cells. The results of this invention suggest that the identified two N-substituted norcantharimide derivatives are potential lead compounds for use as therapeutic agents for treating cancers.

Accordingly, the first aspect of this disclosure is directed to a compound of formula (I),

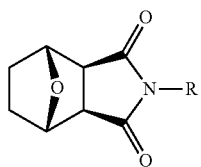

(I)

wherein R is farnesyl or farnesyloxy.

In one example, the compound of formula (I) is N-farnesyloxy-7-oxabicyclo[2.2.1]heptane-2,3-dicarboximide (NOC15). In another example, the compound of formula (I) is N-farnesyl-7-oxabicyclo[2.2.1]heptane-2,3-dicarboximide (NC15).

The second aspect of this disclosure is therefore directed to a pharmaceutical composition for treating cancer. The pharmaceutical composition includes an effective amount of the compound of formula (I) described above; and a pharmaceutically acceptable excipient.

The cancer that may be treated by the pharmaceutical composition of the present disclosure is selected from the group consisting of leukemia, hepatic cancer, bladder cancer, colon cancer, kidney cancer, ovarian cancer, cervical cancer, endometrial carcinoma, prostate cancer, pancreatic cancer, lung cancer, breast cancer, melanoma, and squamous cell carcinoma (SCC). In one example, the cancer is leukemia. In another example, the cancer is hepatic cancer.

The compound of this invention (i.e., the compound of formula (I)) is present at a level of about 0.1% to 99% by weight, based on the total weight of the pharmaceutical composition. In some embodiments, the compound of this invention is present at a level of at least 1% by weight, based on the total weight of the pharmaceutical composition. In certain embodiments, the compound of this invention is present at a level of at least 5% by weight, based on the total weight of the pharmaceutical composition. In still other embodiments, the compound of this invention is present at a level of at least 10% by weight, based on the total weight of the pharmaceutical composition. In still yet other embodiments, the compound of this invention is present at a level of at least 25% by weight, based on the total weight of the pharmaceutical composition.

In some embodiments, the medicament or pharmaceutical composition further comprises another agent that is known to improve the treatment of cancer or help suppress the growth of cancerous cells. Preferably, the medicament or the pharmaceutical composition of this invention further includes a chemotherapeutic agent.

It is therefore the third aspect of this disclosure to provide a method of treating a subject having or suspected of having a cancer. The method includes the step of, administering to the subject the pharmaceutical composition of the present disclosure, so as to suppress or inhibit the growth of the cancer. The cancer treatable by the present method is any of leukemia, hepatic cancer, bladder cancer, colon cancer, kidney cancer, ovarian cancer, cervical cancer, endometrial carcinoma, prostate cancer, pancreatic cancer, lung cancer, breast cancer, melanoma, or squamous cell carcinoma (SCC). In one example, the cancer is leukemia. In another example, the cancer is hepatic cancer. The subject may be a mammal, preferably a human.

In some embodiments, the method further comprises administering to the subject another agent that is known to improve the treatment of cancer before, together with and/or after administering the compound of formula (I). In some examples, the present pharmaceutical composition is administered together with a chemotherapeutic agent.

The details of one or more embodiments of the invention are set forth in the accompanying description below. Other features and advantages of the invention will be apparent from the detail descriptions, and from claims.

It is to be understood that both the foregoing general description and the following detailed description are by examples, and are intended to provide further explanation of the invention as claimed.

BRIEF DESCRIPTION OF THE DRAWINGS

The present description will be better understood from the following detailed description read in light of the accompanying drawings, wherein:

FIGS. 5A to 5C illustrate the cell cycle distribution of human leukemia cells (Jurkat T cells) treated with NOC15 for (A) 0, (B) 24 and (C) 48 hours, respectively in accordance with one embodiment of this invention;

FIG. 5D illustrates the quantitated results from FIGS. 5A to 5C;

FIG. 8A illustrates the survival time course of animals bearing SC-injected L1210 cells treated with NOC15 or NC15 in accordance with one embodiment of this invention;

FIG. 8B illustrates the survival time course of animals bearing IP-injected L1210 cells treated with NOC15 or NC15 in accordance with one embodiment of this invention;

DETAILED DESCRIPTION

Figure 1:
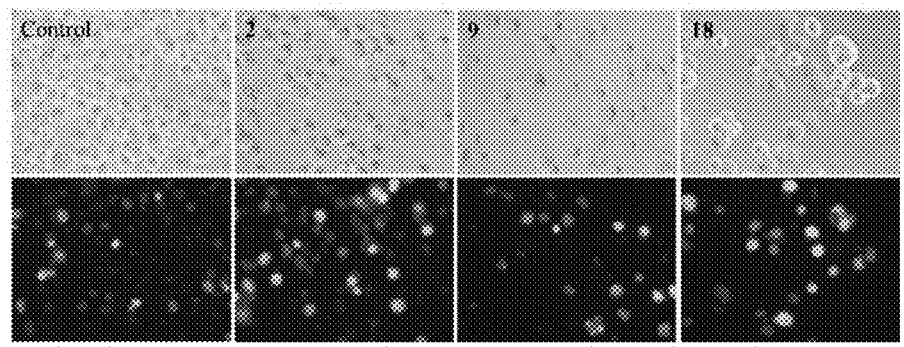
FIG. 1 are photographs of HepG2 cells stained with Hoechst 33528 to revel the nuclear changes unpon being treated with compounds 2, 9 and 18, respectively, in accordance with one embodiment of this invention.

The detailed description provided below in connection with the appended drawings is intended as a description of the present invention and is not intended to represent the only forms in which the present invention may be constructed or utilized.

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attaching claims are approximations that can vary as desired. At the very least, each numerical parameter should at least be construed in light of the number of reported significant digits and by applying ordinary rounding techniques.

The term "inhibiting or inhibition" or "suppress or suppression" as used herein refers to administering a compound of this invention to arrest the growth of at least 45%, 50%, 55%, 60%, 65%, 70%, 75%, 80%, 85%, 90%, 95% or 99% of the cancerous cells, preventing them from multiplying, and hence results in the reduction of the size of the cancer; thus the term "inhibiting or inhibition" or "suppress or suppression" as used herein also refers to kill or induce apoptosis of the cancerous cells.

As used herein, the term "treating" encompasses partially or completely preventing, ameliorating, mitigating and/or managing a symptom, a secondary disorder or a condition associated with tumor. The term "treating" as used herein refers to application or administration of the compound of formula (I) in accordance with the present disclosure, to a subject, who has a symptom, a secondary disorder, or a condition associated with a tumor, with the purpose to partially or completely alleviate, ameliorate, relieve, delay onset of, inhibit progression of, reduce severity of, and/or reduce incidence of one or more symptoms, secondary disorders or features of the tumor. Symptoms, secondary disorders, and/or conditions associated with tumors include, but are not limited to, unexplained weight loss, fever, fatigue, pain, and change in physical function. Treatment may be administered to a subject who exhibits only early signs of such symptoms, disorder, and/or condition for the purpose of decreasing the risk of developing the symptoms, secondary disorders, and/or conditions associated with tumors. Treatment is generally "effective" if one or more symptoms or clinical markers are reduced as that term is defined herein. Alternatively, a treatment is "effective" if the progression of a symptom, disorder or condition is reduced or halted.

The term "an effective amount" as used herein refers to an amount effective, at dosages, and for periods of time necessary, to achieve the desired therapeutically desired result with respect to the treatment of cancer.

The terms "compounds", "compositions", "agent" or "medicament" are used interchangeably herein to refer to a compound or compounds or composition of which, when administered to a subject (human or animal) induces a desired pharmacological and/or physiological effect by local and/or systemic action.

The term "administered", "administering" or "administration" are used interchangeably herein to refer means either directly administering a compound or a composition of the present invention, or administering a prodrug, derivative or analog which will form an equivalent amount of the active compound within the body.

The term "subject" or "patient" refers to an animal including the human species that is treatable with the compositions and/or methods of the present invention. The term "subject" or "patient" intended to refer to both the male and female gender unless one gender is specifically indicated. Accordingly, the term "subject" or "patient" comprises any mammal, preferably a human, which may benefit from treatment by the compound of this disclosure.

The present disclosure is based, at least in part, unexpected discovery that two lipophilic N-substituted norcantharimide derivatives may retard the growth of cancerous cells, particularly leukemia cancer cells, without affecting the normal cells. Therefore, these two N-substituted norcantharimide derivatives are potential lead compounds for use as therapeutic agents for treating cancers, including leukemia.

One aspect of the present disclosure is therefore directed to a compound of formula (I),

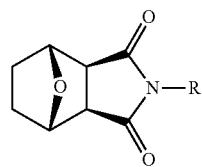

wherein R is farnesyl or farnesyloxy

In one preferred example, the compound of formula (I) is N-farnesyloxy-7-oxabicyclo[2.2.1]heptane-2,3-dicarboximide (Compound 9 or NOC15). In another preferred example, the compound of formula (I) is N-farnesyl-7-oxabicyclo[2.2.1]heptane-2,3-dicarboximide (Compound 18 or NC15).

NOC15 and NC15 may be respectively produced by following steps as defined in respective synthetic schemes set forth in example 1 of the present disclosure.

According to one embodiment, scheme 1 is employed for the production of NO-substituted norcantharimide derivatives, including NOC15. Specifically, 5,6-dehydronorcantharididn (5) is first produced by following a Diels-Alder reaction using furan (3) and maleic anhydride (4) as the starting materials. Then, compound 5 is hydrogenated to give norcantharidin (2), which is then reacted with hydroxylamine hydrochloride in the presence of sodium methoxide in dry methanol at room temperature to produce N-hydroxynorcantharimide (6). N-hydroxynorcantharimide (6) is then reacted with farnesyl bromide in the presence of $K_2CO_3$ to produce N-farnesyloxy-7-oxabicyclo[2.2.1]heptane-2,3-dicarboximide (Compound 9 or NOC15).

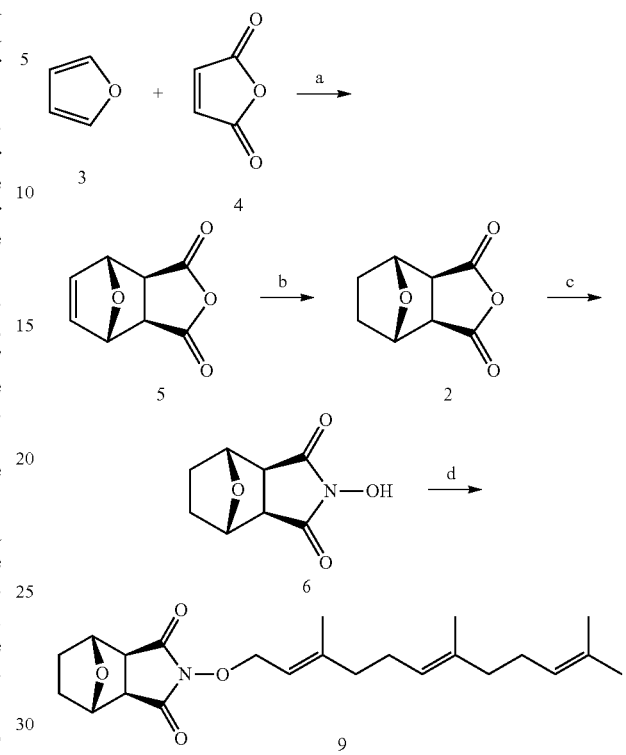

Scheme 1. Synthesis of NOC15.

Reagents and conditions in Scheme 1 are as follows: (a) Ether, room temperature, 48 hrs; (b) 3 atm $H_2$, 10% Pd/C, THF, room temperature, 8 hrs; (c) $NaOCH_3$, $NH_2OH \cdot HCl$, MeOH, room temperature, 20 hrs; (d) $K_2CO_3$, farnesyl bromide, acetone, reflux, 8-10 hrs.

According to another embodiment, scheme 2 is employed for the production of N-substituted norcantharimide derivatives, including NC15. Scheme 2 begins by letting furan (3) and maleimide (13) react in toluene to give dihydroxynorcantharimide (14), which is then hydrogenated to generate norcantharimide (15). Then, norcantharimide (15) is reacted with farnesyl bromide in the presence of $K_2CO_3$ to produce N-farnesyl-7-oxabicyclo[2.2.1]heptane-2,3-dicarboximide (Compound 18 or NC15).

Scheme 2. Synthesis of NC15.

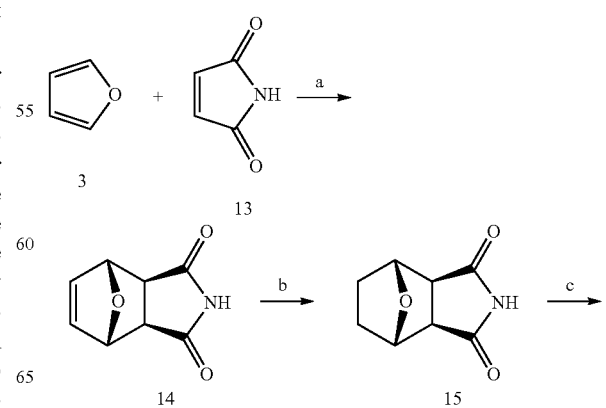

-continued

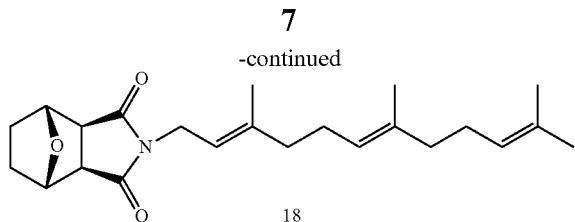

18

Reagents and conditions in Scheme 2 are as follows: (a) Toluene, 80° C., 6 hrs; (b) 3 atm $H_2$, 10% Pd/C, THF, room temperature, 8-48 hrs; (c) $K_2CO_3$, farnesyl bromide, acetone, reflux, 8-10 hrs.

The growth of cancerous cells, such as leukemia, hepatic cancer, bladder cancer, colon cancer, kidney cancer, ovarian cancer, cervical cancer, endometrial carcinoma, prostate cancer, pancreatic cancer, lung cancer, breast cancer, melanoma, and squamous cell carcinoma (SCC), may be inhibited or suppressed by the compound of formula (I) at a concentration from about 1 to 20 μM, such as 1, 2, 3, 4, 5, 6, 7, 8, 9, 10, 11, 12, 13, 14, 15, 16, 17, 18, 19 or 20 μM. In one example, the ex vivo growth of hepatic cancerous cells is inhibited for about 50% at about 8.2 μM of NOC15 (compound 9); while the normal hepatic cells remain un-affected. In still another example, the ex vivo growth of hepatic cancerous cells is inhibited by NOC15 (compound 9) for about 50% at a concentration of about 10.7 μM. In a further example, the ex vivo growth of leukemia cells is suppressed for about 50% by about 8.3 μM. In still another example, the ex vivo growth of leukemia cells (L1210) is suppressed for about 50% by about 1.6 μM NC15 (compound 18). In other example, the ex vivo growth of L1210 cells is suppressed for about 50% by about 2.6 μM NC15 (compound 18).

Accordingly, this disclosure provides a pharmaceutical composition suitable for treating cancer, which includes, but is not limited to, leukemia, hepatic cancer, bladder cancer, colon cancer, kidney cancer, ovarian cancer, cervical cancer, endometrial carcinoma, prostate cancer, pancreatic cancer, lung cancer, breast cancer, melanoma, and squamous cell carcinoma (SCC). In one preferred example, the cancer is leukemia. In another preferred example, the cancer is hepatic cancer.

The pharmaceutical composition comprises an effective amount of the compound of formula (I); and a pharmaceutically acceptable excipient. Generally, the compound of formula (I) is present at a level of about 0.1% to 99% by weight, based on the total weight of the pharmaceutical composition. In some embodiments, the compound of formula (I) is present at a level of at least 1% by weight, based on the total weight of the pharmaceutical composition. In certain embodiments, the compound of formula (I) is present at a level of at least 5% by weight, based on the total weight of the pharmaceutical composition. In still other embodiments, the compound of formula (I) is present at a level of at least 10% by weight, based on the total weight of the pharmaceutical composition. In still yet other embodiments, the compound of formula (I) is present at a level of at least 25% by weight, based on the total weight of the pharmaceutical composition.

The pharmaceutical compositions of this invention may be prepared in accordance with acceptable pharmaceutical procedures, such as described in Remington's Pharmaceutical Sciences, 17$^{th}$ edition, ed. Alfonoso R. Gennaro, Mack Publishing Company, Easton, Pa. (1985). Pharmaceutically acceptable excipients are those that are compatible with other ingredients in the formulation and biologically acceptable.

The pharmaceutical composition may be formulated into solid dosage forms include, but are not limited to, tablets, capsules, and sachets. Each tablet may contain various excipients such as microcrystalline cellulose, sodium citrate, calcium carbonate, dicalcium phosphate, and glycine; along with various disintegrants such as starch, alginic acid and certain silicates; together with granulation binders like polyvinylpyrrolidone, sucrose, gelatin and *acacia*. Additionally, lubricating agents such as magnesium stearate, sodium lauryl sulfate and talc may be added. Materials in this connection also include lactose or milk sugar as well as high molecular weight polyethylene glycols. The described solid dosage forms may optionally contain coatings and shells, such as enteric coatings, and coatings for modifying the release rate of any of the ingredients. Examples of such coatings are well known in the art. In one example, the pharmaceutical compositions of this disclosure are formulated into tablets. In another example, the pharmaceutical compositions of this disclosure are powders that are encapsulated in soft and hard gelatin capsules or packed in biodegradable pharmaceutical sachets. When aqueous suspensions and/or elixirs are desired for oral administration, the active ingredient may be combined with various sweetening or flavoring agents, coloring matter or dyes, and if so desired, emulsifying and/or suspending agents as well, together with diluents such as water, ethanol, propylene glycol, glycerin and a combination thereof.

In some embodiments, the pharmaceutical compositions of this disclosure are liquid dosage forms for oral administration. The liquid formulation may further include a buffering agent to maintain a desired pH. The liquid dosage formulations may also be filled into soft gelatin capsules. For example, the liquid may include a solution, suspension, emulsion, microemulsion, precipitate or any desired liquid media carrying the compound of formula (I), a pharmaceutically acceptable derivative, stereoisomer, metabolite, salt or solvate thereof, or a combination thereof. The liquid may be designed to improve the solubility of the compound of formula (I) to form a drug-containing emulsion or disperse phase upon release. In such forms, the active ingredient is mixed with at least one pharmaceutically acceptable excipient including, but is not limited to, as described above.

In some embodiments, the pharmaceutical compositions of this disclosure are liquid dosage forms for parenteral administration, which are sterile solutions, or suspensions that can be administered by, for example, intravenous, intramuscular, subcutaneous, or intraperitoneal injection. Suitable diluents or solvent for manufacturing sterile injectable solution or suspension include, but are not limited to, 1,3-butanediol, mannitol, water, Ringer's solution, and isotonic sodium chloride solution. Fatty acids, such as oleic acid and its glyceride derivatives are also useful for preparing injectables, as are natural pharmaceutically-acceptable oils, such as olive oil or castor oil. These oil solutions or suspensions may also contain alcohol diluent or carboxymethyl cellulose or similar dispersing agents. Other commonly used surfactants such as Tweens or Spans or other similar emulsifying agents or bioavailability enhancers that are commonly used in manufacturing pharmaceutically acceptable dosage forms can also be used for the purpose of formulation.

In some other embodiments, the pharmaceutical compositions of this disclosure are liquid dosage forms for transmucosal administration, the medicament or said pharmaceutical compositions of this invention may also be formulated in a variety of dosage forms for mucosal application, such as buccal and/or sublingual drug dosage units for drug delivery through oral mucosal membranes. A wide variety of biodegradable polymeric excipients may be used that are pharmaceutically acceptable, provide both a suitable degree of adhesion and the desired drug release profile, and are compatible with the active agents to be administered and any other components that may be present in the buccal and/or sublingual drug dosage units. Generally, the polymeric excipient comprises hydrophilic polymers that adhere to the wet surface of the oral mucosa. Examples of polymeric excipients include, but are not limited to, acrylic acid polymers and copolymers; hydrolyzed polyvinylalcohol; polyethylene oxides; polyacrylates; vinyl polymers and copolymers; polyvinylpyrrolidone; dextran; guar gum; pectins; starches; and cellulosic polymers.

In addition, the pharmaceutical compositions of this invention may also be formulated into a variety of dosage forms for topical application, a wide variety of dermatologically acceptable inert excipients well known to the art may be employed to prepare the pharmaceutical compositions of this invention. The topical compositions may include liquids, creams, lotions, ointments, gels, sprays, aerosols, skin patches, and the like. Typical inert excipients may be, for example, water, ethyl alcohol, polyvinyl pyrrolidone, propylene glycol, mineral oil, stearyl alcohol and gel-producing substances. All of the above dosages forms and excipients are well known to the pharmaceutical art. The choice of the dosage form is not critical to the efficacy of the composition described herein.

Accordingly, the present disclosure also provides a method of treating a subject having or suspected of having cancer. The method includes, administering to the subject the pharmaceutical composition of the present disclosure that comprises an effective amount of the compound of formula (I), so as to suppress and/or inhibit the growth and/or metastasis of the cancer. Examples of cancer treatable by the present method include, but are not limited to, leukemia, hepatic cancer, bladder cancer, colon cancer, kidney cancer, ovarian cancer, cervical cancer, endometrial carcinoma, prostate cancer, pancreatic cancer, lung cancer, breast cancer, melanoma, and squamous cell carcinoma (SCC). In one preferred example, the subject has leukemia. In another preferred example, the subject has hepatic cancer.

In some embodiments, the present pharmaceutical composition, which comprises an effective amount of the compound of formula (I), is administered to the subject from about 1 to 100 mg/Kg body weight of the subject by oral ingestion, intravenous or intramuscular injection. Preferably, the present composition is administered orally. The amount is administered to the subject at about 1, 5, 10, 20, 30, 40, 50, 60, 70, 80, 90 or 100 mg/Kg body weight of the subject per day, preferably about 30 to 70 mg/Kg body weight of the subject, such as 30, 40, 50, 60 or 70 mg/Kg body weight of the subject per day; and more preferably about 50 mg/Kg body weight of the subject per day. The dose can be administered in a single dosage, or alternatively in more than one dosage.

In some embodiments, the method further includes the step of administering another agent that is known to improve the treatment of cancer, before, together with and/or after administering the present pharmaceutical composition (or the compound of formula (I) of this invention). The agent that may be administered with the present composition or the compound of formula (I) is a chemotherapeutic agent such as an alkylating agent, a topoisomerase inhibitor, a cytotoxic agent, an anti-microtubule agent and etc.

In general, the present composition (or the compound of formula (I)) may be administered by any suitable route, for example, orally in capsules, sachets, suspensions or tablets; or by parenterally administration. Parenterally administration can include, for example, systemic administration such as oral, intramuscular, intravenous, subcutaneous, or intraperitoneal injection. The composition can also be administered transdermally either topically or by inhalation (e.g., intrabronichial, intranasal, oral inhalation or intranasal drops), or rectally, alone or in combination with conventional pharmaceutically acceptable excipients. In preferred embodiments, the present composition is administered orally (e.g., dietary) to the subject.

In some preferred embodiments, the subject receiving the present composition exhibits at least 10% to 40% increases in life span, a reduction in the tumor size and in the white blood cell counts, as compared with any of that of a control subject (i.e., the subject without being treated by the preset composition).

It will be appreciated that the dosage of compounds of the present invention will vary from patient to patient not only for the particular compound or composition selected, the route of administration, and the ability of the compound (alone or in combination with one or more drugs) to elicit a desired response in the patient, but also factors such as disease state or severity of the condition to be alleviated, age, sex, weight of the patient, the state of being of the patient, and the severity of the pathological condition being treated, concurrent medication or special diets then being followed by the patient, and other factors which those skilled in the art will recognize, with the appropriate dosage ultimately being at the discretion of the attendant physician. Dosage regimens may be adjusted to provide the improved therapeutic response. A therapeutically effective amount is also one in which any toxic or detrimental effects of the compound or composition are outweighed by the therapeutically beneficial effects. Preferably, the compounds or compositions of the present invention are administered at a dosage and for a time such that the number and/or severity of the symptoms are decreased.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in the respective testing measurements.

The present invention will now be described more specifically with reference to the following embodiments, which are provided for the purpose of demonstration rather than limitation.

Examples

Materials and Methods

Cell Culture and Animals

Cell lines used in the present disclosure include human liver carcinonoma cell line HepG2, human bladder carcinoma cell line BFTC905, human colon carcinoma cell lines HT29 and SW480, and human leukemia cell lines HL60 and Jurkat T, and mouse lymphocytic leukemia cell line L1210. Each cell lines were cultured and maintained in Dulbecco's modified Eagle media (DMEM) or RPMI 1640 medium supplemented with 10% heat inactivated fetal bovine serum (FBS), 1% penicillin/streptomycin, in 5% $CO_2$/95% air at 37° C.

The DBA/2 mice (about 7 weeks old, 18-22 g) were obtained from BioLASCO Taiwan Co., Ltd. All mice were housed in specific pathogen-free condition with ad libitum access to water and laboratory chow. A solution of L1210 cells was injected into the subcutaneous tissue to establish a syngeneic tumor. Alternatively, the L1210 cells was injected peritoneally. All animal experiments were performed in accordance with the guidelines of the Animal Welfare Committee of Taipei Veterans General Hospital (Taiwan, R.O.C.).

MTT Assay

MTT assay is a colorimetric assay that measures the activity of enzymes (i.e., reductase) that reduce (3-(4,5-dimethylthiazol-2yl)-2,5-diphenyltetrazoliumbromide (MTT), a yellow tetrazole, to purple formazan, in living cells. This reduction only takes place when cells are alive; hence MTT assay is generally used to assess the viability and proliferation of cells. Briefly, cells were challenged with various doses of the tested compound (e.g., the compound of formula (I)) for 48 hours. Then, MTT dye (5 mg/ml, 10 μL) was added and the reaction was allowed to proceed for 1 hour before being terminated by the addition of 500 μl of isopropanol. The absorbance of the solution at 540 nm was measured by spectrophotometer. The $IC_{50}$ values were defined as the drug concentration that inhibit 50% cell growth by setting the viability of untreated cells as 100%. Values were represented as the mean±SD from at least 3 independent experiments.

Phorbol 12-Myristate 13-Acetate Plus Ionomycin (PMAI) Activated Leukemia Jurkat T Cells Model The cell viability assays were performed in 96-well plates. The 100 μl of cell suspensions (NHL or Jurkat T cells, $5 \times 10^3$ cells/well, serum-free medium) were inoculated in the wells and the plates were pre-incubated in the incubator for 24 hours (pre-incubated for 22 hours and stimulated with PMA 5 ng/ml plus ionomycin 250 ng/ml for 2 hours in PMAI-treated groups). Then, various concentrations of norcantharidin (0, 2, 4, 15, 30 and 60 μM) or NOC15 (0, 0.25, 0.5, 1, 2 and 4 μM) were added into the culture media in the wells. After 24 hours of incubation, the cell viability of NHL and Jurkat T cells was measured by cell counting kit-8 (CCK-8, Sigma). The half maximal inhibitory concentrations ($IC_{50}$) of norcantharidin and NOC15 on Jurkat T cells and NHL cells were calculated.

Hoechst 33528 Staining

Staining with Hoechst 33528 was performed according to the method described previously (Huang et al., Cytotechnology 2009, 59, 201-208). Briefly, cells were treated with 40 μM norcantharidin, NOC15, or NC15 for 48 hours, then washed with PBS saline and stained with Hoechst 33528 (Sigma, St. Louis, Mo., USA) at a final concentration of 10 μg/mL. The slides were examined under a fluorescence microscope. Cells with a small nucleus, a high fluorescence intensity (due to chromatin condensation) or nuclear fragmentation were considered apoptotic.

Cell Cycle Analysis

Cultured cells with or without pre-treatment of the compounds of this invention (i.e., norcantharidin, NOC15, or NC15, 10-60 μM for 48 hours) were harvested from the cultured media and fixed by incuating with 75% iced cold ehtanol and kept at −20° C. until analysis. The fixed cells were then washed with PBS, and treated with DNAase (200 μg/mL, 500 μL) for about 1.5 hour at 37° C. Precipitated cells were collected by centrifugation and re-suspended in a buffer solution containing propidium iodine (PI) (40 μg/ml) and incubated in the dark for 20 min at 20-25° C. before being subject to flow cytometry analysis, where cell numbers at respective cell cycles were determined.

The percentage of apotoptic cells was determined according to the manufacturer's protocol by using an annexin-V/FITC kit/propidium iodine (PI) flow cytometer. To facilitate the detection of apoptosis, the treated cells were centrifuged for 5 min at a speed of 1,000×g at room temperature, and then resuspended and washed once with 5 mL PBS before being stained with annexin-V/PI (apoptosis detection kit, R&D Systems, Taipei, Taiwan).

Syngeneic Tumor Generation and In Vivo Therapy

To inoculate tumor, L1210 cells ($1 \times 10^6$ cells per injection) were injected either subcutaneously or intraperitoneally to lab animals to generate tumors on day 1. After 7 days, NOC15 or NC15 (diluted in normal saline) was administered intraperitoneally at a dose of 18 mg/kg every day for 7 days. The average body weight (BW) of the animals was measured daily.

After treatment, mice were sacrificed, and their tumors, livers and spleens were harvested and weighted, respectively; and white blood cells (WBC) counts were also measured.

Example 1

Synthesis of the Compound of the Present Invention 1.1 Production of N-farnesyloxy-7-oxabicyclo[2.2.1]heptane-2,3-dicarboximide (Compound 9 or NOC15)

NOC15 was synthesized in accordance with following scheme I.

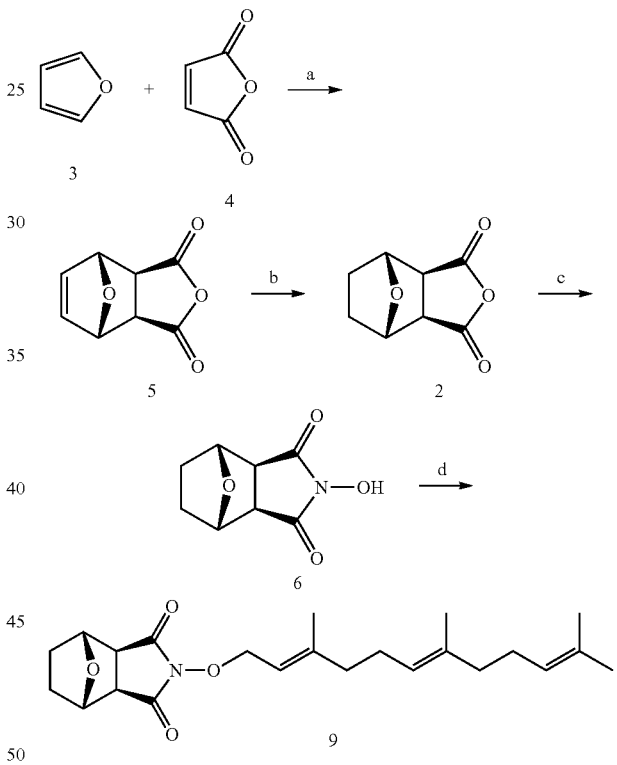

Reagents and conditions in Scheme 1 are as follows: (a) Ether, room temperature, 48 hrs; (b) 3 atm $H_2$, 10% Pd/C, THF, room temperature, 8 hrs; (c) $NaOCH_3$, $NH_2OH\cdot HCl$, MeOH, room temperature, 20 hrs; (d) $K_2CO_3$, farnesyl bromide, acetone, reflux, 8-10 hrs.

7-oxabicyclo[2.2.1]-5-heptene-2,3-dicarboxylic anhydride (Compound 5)

A solution of furan (40 mL, 550 mmol) and maleic anhydride (10 g, 102 mmol) were mixed in ether (100 mL) and reacted at room temperature for 48 hours, after which the white precipitate was collected, and dried to produce compound 5 as a colorless solide, yield 93.3%, mp 121-122° C. $^1H$ NMR ($CDCl_3$) δ 6.58 (5, 2H, H-5,6), 5.47 (5, 2H, H-1,4), 3.19 (5, 2H, H-2,3); $^{13}C$ NMR ($CDCl_3$) δ 170.1 (C=O), 137.2

(C-5, C-6), 82.4 (C-1, C-4), 48.9 (C-2, C-3); LC-MS (ESI⁻, m/z) calculated for $C_8H_6O_4$: 166.03. found for 164.90 [M-H]⁻.

7-oxabicyclo[2.2.1]heptane-2,3-dicarboxylic anhydride (Compound 2)

To a solution of compound 5 (4.7 g, 28.3 mmol) in tetrahydrofuran (THF) (200 mL), 10% Pd/C (470 mg) was added, and the mixture was stirred at room temperature under a hydrogen atmosphere (3 atm) for 8-12 hours. The reaction mixture was filtered through Celite 545 and concentrated under vaccum condition to give compound 2 (i.e., norcantharidin) as colorless crystals, yield 91.4%, mp 116-118° C. ¹H-NMR (CDCl₃): δ 5.05 (t, J=2.3 Hz, 2H, H-1, 4), 3.18 (5, 2H, H-2,3), 1.91-1.89 (m, 2H, H-5,6), 1.65-1.63 (m, 2H, H-5,6); ¹³C-NMR (CDCl₃): δ 171.7, 80.2, 50.6, 28.1; LC-MS (ESI⁻, m/z) calculated for $C_8H_8O_4$: 168.04. found for 166.86 [M-H]⁻.

N-hydroxy-7-oxabicyclo[2.2.1]-5-heptene-2,3-dicarboximide (Compound 6)

In a solution of compound 2 (5.04 g, 30 mmol) in dry methanol (200 mL), sodium methoxide (1.62 g, 30 mmol) and hydroxylamine hydrochloride (2.08 g, 30 mmol) were added, and the mixture was stirred at room temperature for 20 hours. The reaction mixture was then filtered and concentrated under vaccum condition, and recrystallized using CHCl₃ to give compound 6 as colorless crystals, yield 63%, mp 168-169° C. ¹H-NMR (D₂O): δ 4.93 (s, 2H, H-1, 4), 3.21 (s, 2H, H-2,3), 1.89-1.86 (m, 2H, H-5,6), 1.78-1.74 (m, 2H, H-5,6); ¹³C-NMR (D₂O): δ 177.0, 78.8, 46.9, 28.0; LC-MS (ESI⁺, m/z) calculated for $C_8H_9NO_4$: 183.05. found for 206.00 [M+Na]⁺.

N-farnesyloxy-7-oxabicyclo[2.2.1]heptane-2,3-dicarboximide (Compound 9 or NOC15)

To a stirred solution of compound 6 (1 mmol) in dry acetone, farnesyl bromide (1 mmol) and K₂CO₃ (3 mmol) were added, and the mixture was refluxed for 8-10 hours. Then, the mixture was filtered and concentrated under vaccum condition, and the residue was purified by column chromatography using silica gel with ethyl acetate/n-hexane as eluent to produce NOC15. Colorless liquid, yield 28%. ¹H-NMR (CDCl₃): δ 5.42 (td, J=0.9, 7.7 Hz, 1H, H-2'), 5.11-5.07 (m, 2H, H-6', 10'), 4.85 (q, J=2.4 Hz, 2H, H-1,4), 4.62 (d, J=7.7 Hz, 2H, H-1'), 2.83 (s, 2H, H-2,3), 2.09-2.04 (m, 6H, H-5,6, H-4',8'), 1.99-1.96 (m, 2H, H-5'), 1.89-1.86 (m, 2H, H-6'), 1.72 (d, J-0.7 Hz, 3H, CH₃), 1.68 (s, 3H, CH₃), 1.63-1.62 (m, 2H, H-5,6), 1.60 (s, 3H, CH₃), 1.59 (s, 3H, CH₃); ¹³C-NMR (CDCl₃): δ 171.6, 147.3, 135.3, 131.3, 124.3, 123.5, 116.1, 78.5, 73.0, 47.4, 39.65, 39.63, 28.7, 26.7, 26.1, 25.7, 17.7, 16.6, 16.0; LC-MS (ESI⁺, m/z) calculated for $C_{23}H_{33}NO_4$: 387.24. found for 410.21 [M+Na]⁺.

1.2 Production of N-farnesyl-7-oxabicyclo[2.2.1]heptane-2,3-dicarboximide (Compound 18 or NC15)

NC15 was synthesized in accordance with following scheme II.

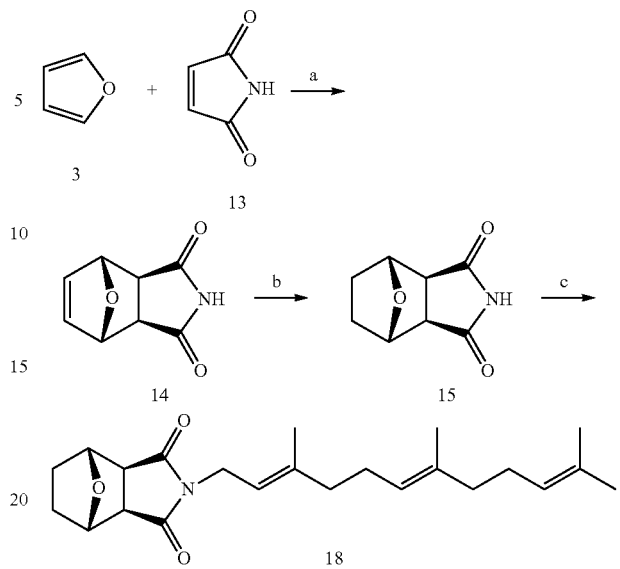

Reagents and conditions in Scheme 2 are as follows: (a) Toluene, 80° C., 6 hrs; (b) 3 atm H₂, 10% Pd/C, THF, room temperature, 8-48 hrs; (c) K₂CO₃, farnesyl bromide, acetone, reflux, 8-10 hrs.

7-Oxabicyclo[2.2.1]-5-heptene-2,3-dicarboximide (Compound 14)

A solution of maleimide (compound 13) (1.5 g, 15 mmol) in dry toluene (30 mL) was heated at 80° C., then furan (5.4 mL, 75 mmol) was added and stirred at 80° C. for 6 hours, cooled to room temperature and white precipitate was collected and purified by column chromatography using silica gel with ethyl acetate/n-hexane as eluent to produce compound 14 (2.1 g, yield 87%) as colorless crystals, mp 162-163° C. ¹H-NMR (CDCl₃): δ 8.13 (s, 1H, NH), 6.50 (s, 2H, H-5,6), 5.29 (s, 2H, H-1.4), 2.87 (s, 2H, H-2,3); ¹³C-NMR (CDCl₃): δ 176.2, 136.8, 81.2, 48.9; LC-MS (ESI⁻, m/z) calculated for $C_8H_7NO_3$: 165.04. found for 164.02 [M-H]⁻.

7-Oxabicyclo[2.2.1]heptane-2,3-dicarboximide (Compound 15)

A solution of compound 14 (0.5 g, 2.8 mmol) in THF (20 mL) was added 10% Pd/C (50 mg), and the mixture was stirred at room temperature under a hydrogen environment for 4 hours. The reaction mixture was filtered through Celite and concentrated under vaccum condition to produce NC15. (424 mg, yield 84%) as colorless crystals, mp 188-190° C. ¹H-NMR (CDCl₃): δ 8.60 (s, 1H, NH), 4.91 (dd, J=2.4, 3.3 Hz, 2H, H-1,4), 2.92 (s, 2H, H-2,3), 1.89-1.85 (m, 2H, H-5,6), 1.61-1.57 (m, 2H, H-5,6); ¹³C-NMR (CDCl₃): δ 177.2, 79.1, 51.3, 28.5; LC-MS (ESI⁻, m/z) calculated for $C_8H_9NO_3$: 167.06. found for 166.03 [M-H]⁻.

N-farnesyl-7-oxabicyclo[2.2.1]heptane-2,3-dicarboximide (Compound 18 or NC15)

In a mixture of compound 15 (1.0 mmol) in dry acetone (25 mL), farnesyl bromide (1 mmol) and K₂CO₃ (3 mmol) were added, and the mixture was refluxed for 8-10 hours. Then, the mixture was filtered and concentrated under vaccum condition, and the residue was purified by column chromatography using silica gel with ethyl acetate/n-hexane as eluent to produce NC15 as colorless liquid, yield 20%. $^1$H-NMR (CDCl$_3$): δ 5.10-5.02 (m, 3H, H-2', 6', 10'), 4.84 (dd, J=2.2, 2.3 Hz, 2H, H-1,4), 4.03 (d, J=7.0 Hz, 2H, H-1'), 2.82 (s, 2H, H-2,3), 2.06-2.01 (m, 4H, H-4',8'), 1.97-1.92 (m, 4H, H-5', 9'), 1.84-1.81 (m, 2H, H-5,6), 1.75 (s, 3H, CH$_3$), 1.67 (s, 3H, CH$_3$), 1.60 (s, 3H, CH$_3$), 1.59 (s, 3H, CH$_3$), 1.58-1.55 (m, 2H, H-5,6); $^{13}$C-NMR (CDCl$_3$): δ 176.8, 140.9, 135.3, 131.2, 124.3, 123.7, 117.2, 78.9, 50.0, 39.7, 39.5, 37.0, 28.6, 26.8, 26.3, 25.7, 17.7, 16.4, 16.0; LC-MS (ESI$^+$, m/z) calculated for C$_{23}$H$_{33}$NO$_3$: 371.25. found for 394.2 [M+Na]$^+$.

Example 2

Anti-Proliferative Activity of the Compounds of this Invention

Effects of the compounds of formula (I) of this disclosure, specifically, NOC15 and NC 15, on HepG2 cells (liver carcinoma), BFTC905 (bladder carcinoma), HT29 (colon carcinoma), SW480 (colon carcinoma) and HL60 (leukemia) were assessed by cell viability analysis in accordance with procedures described above, in which compound 2, and other known anti-cancer agents including 5-FU, cisplatin and doxorubicin were respectively used as positive controls. Results are summarized in Table 1.

TABLE 1

Growth Inhibition On Various Cancer Cell Lines

| Compound | IC$_{50}$ (µM) (Mean ± SD) | | | | |
|---|---|---|---|---|---|
| | HepG2 | BFTC905 | HT-29 | SW480 | HL-60 |
| Compound 2 | 42.0 ± 1.8 | 18.9 ± 0.3 | 19.5 ± 0.2 | 49.1 ± 8.4 | ND |
| Compound 9 (NOC15) | 8.3 ± 1.3 | 11.3 ± 1.0 | 9.7 ± 1.7 | 18.5 ± 2.3 | 39.0 ± 1.1 |
| Compound 18 (NC15) | 16.4 ± 1.2 | 9.3 ± 0.6 | 14.8 ± 1.9 | 33.1 ± 1.0 | 79.8 ± 1.1 |
| 5-FU | 40.2 ± 7.6 | ND | ND | 32.7 ± 8.3 | ND |
| Cisplatin | 36.1 ± 3.1 | —$^a$ | 24.1 ± 0.1 | 40.7 ± 1.2 | ND |
| Doxorubicin | 0.3 ± 0.0 | —$^a$ | 1.7 ± 0.2 | 0.5 ± 0.1 | 14.3 ± 0.9 |

$^a$Not tested.
ND indicated that no apprecible inhibition value (IC$_{50}$) was observed upon treatment of maximum concentration at 100 µM.

As evident from data presented in Table 1, both NOC15 and NC15 were cytotoxic to the 5 different types of cancer cell lines, including liver, bladder, colon, and leukemia cancer cells; and each compound was at least as potent, or even more potent, than the other known anti-cancer agents, such as 5-FU, cisplatin and doxorubicin. It was further noted that leukemia cell line HL60 did not respond well to the treatment of 5-FU or cisplatin, but did respond to the treatment of NOC15 or NC15.

Example 3

Anti-Proliferative Activities of NOC15 and NC15 on Human Hepatic Cancer

3.1 Cell Viability Analysis

In this example, effects of NOC15 or NC15 on HepG2 cells were assessed by cell viability analysis in accordance with procedures described above, in which compound 2 was used as a positive control. Results are summarized in Table 2.

TABLE 2

Growth Inhibition On Hepatic Cancer Cells

| Compound | IC$_{50}$ (µM) (Mean ± SD) | | |
|---|---|---|---|
| | 24 hrs | 48 hrs | 72 hrs |
| Compound 2 | 48.0 ± 0.7 | 42.0 ± 1.8 | 22.8 ± 0.6 |
| Compound 9 (NOC15) | 10.7 ± 0.2*** | 8.3 ± 1.3*** | 8.2 ± 0.6*** |
| Compound 18 (NC15) | 19.43 ± 2.1** | 16.4 ± 1.2*** | 12.8 ± 2.5*** |

**p < 0.01,
****P < 0.001 versus compound 2.

It is evident from Table 2, NOC15 and NC 15 were respectively at least 3 to 4 times more potent than compound 2, in which same level of inhibition in terms of the reduction in cell number was achieved at ⅓ to ¼ of the dose of compound 2.

3.2 Nuclear morphological changes

To further investigate the role of apoptosis in the cytotoxicity of NOC15 and NC15, HepG2 cells were incubated with compound 2, NOC15 and NC15, respectively, for 48 hours; then were stained with Hoechst 33528 and examined by fluorescence microscope for any topical morphological changes.

The photographs in FIG. 1 depict the nuclei of cells treated with compound 2, NOC15 and NC15, respectively. Significant morphological features of apotosis, including cell shrinkage, chromatin condensation and DNA fragmentation, were found in the treated cells (including compound 2, NOC15, and NC15), as compared with those of control cells.

3.3 Cell Cycle Distribution and Apoptotic Analysis

HepG2 cells were treated with 10-60 µM of the test compounds for 48 hours, then cell cycle distribution and apoptosis analysis was analyzed by flow cytometry, with the subG1 phase being stained with propidium idoine (PI). Results are illustrated in FIGS. 2 and 3.

Figure 2:
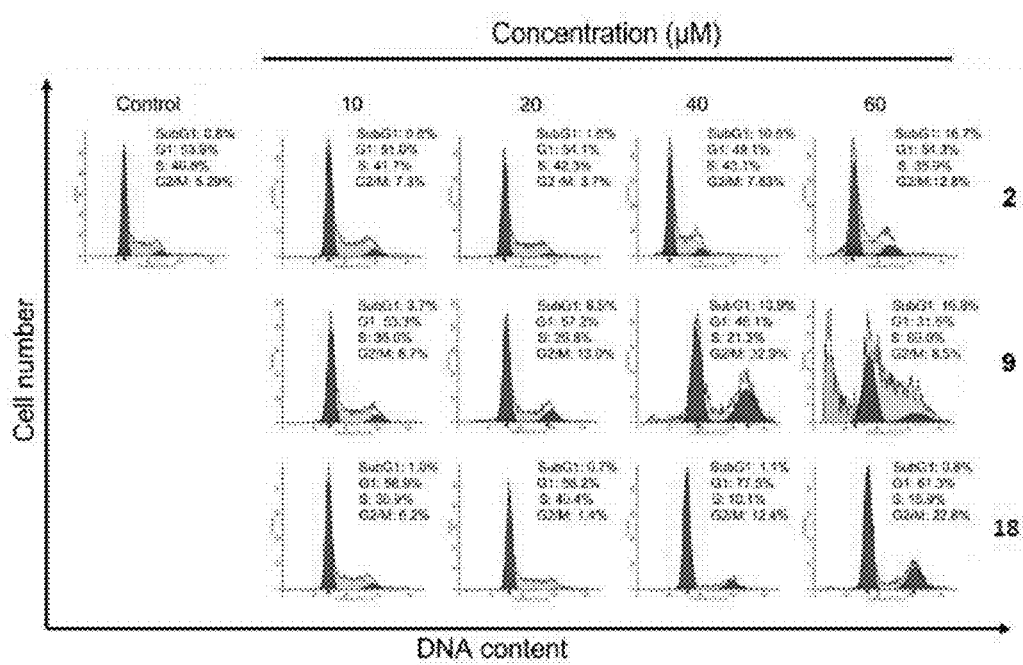
FIG. 2 illustrates the cell cycle analysis of HepG2 cells upon being treated with compounds 2, 9 and 18, respectively, in accordance with one embodiment of this invention.

As depicted in FIG. 2, only a small fraction of apoptotic cells were detected in the control cells (i.e., without treatment) as well as in low concentration (i.e., 10 µM) compound 2 treated cells. As the concentration of compound 2 increased from 20 µM to 60 µM, the fraction of apoptotic cell increased from 1.6% to 16.7% in a dose-dependent manner. Similarly, significant fraction of apoptotic cells was found when cells were treated with increased concentration of compound 18 from 10 µM to 60 µM (3.7% to 19.8%). Further, both compounds 9 and 18 (i.e., NOC15 and NC15) were capable of inducing the accumulation of cells in G2/M phase.

Figure 3:
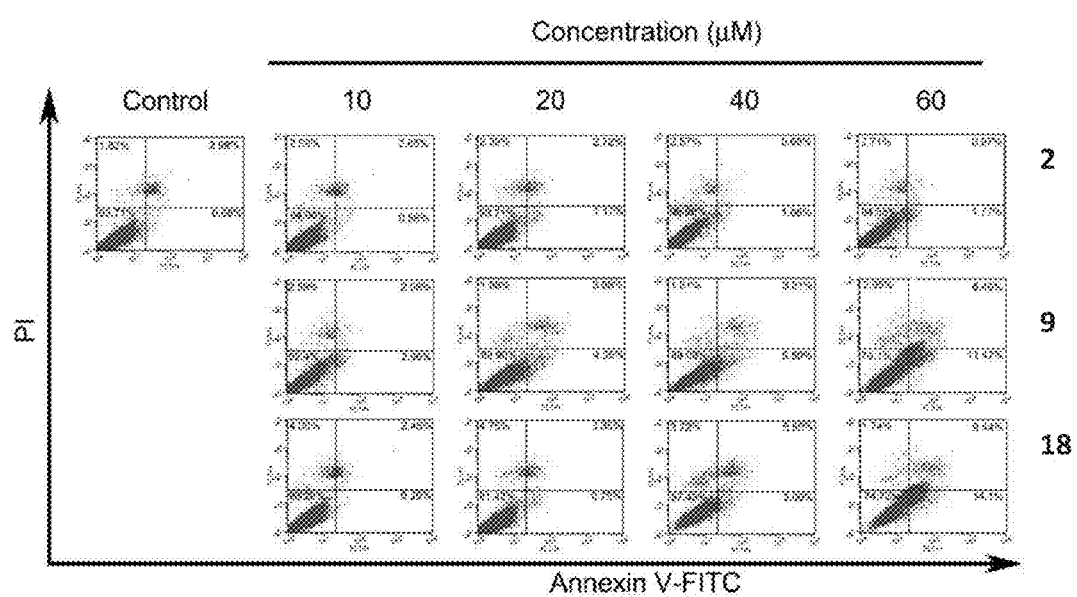
FIG. 3 illustrates the apoptotic analysis of cells upon being treated with compounds 2, 9 and 18, respectively, in accordance with one embodiment of this invention.

As evident from the data depicted in FIG. 3, cell death resulted from the treatment of NOC15 or NC15 appeared to be dose-dependent, the percentage of apoptotic cells increased with an increase in the concentration of NOC15 or NC 15. As to compound 2, cytoxic effect was only observed when high concentration of compound 2 was used (i.e., 60 µM).

Example 4

Anti-Proliferative Activities of NOC15 on Leukemia

4.1 Cell Viability Analysis

In this example, a model of phorbol 12-myristate 13-acetate plus ionomycin (PMAI) activated leukemia Jurkat T cells model was employed to investigate the effects of the NOC15 on human leukemia cells (Jurkat T cells) and human lymphoblast cells (NHL).

Figure 4:
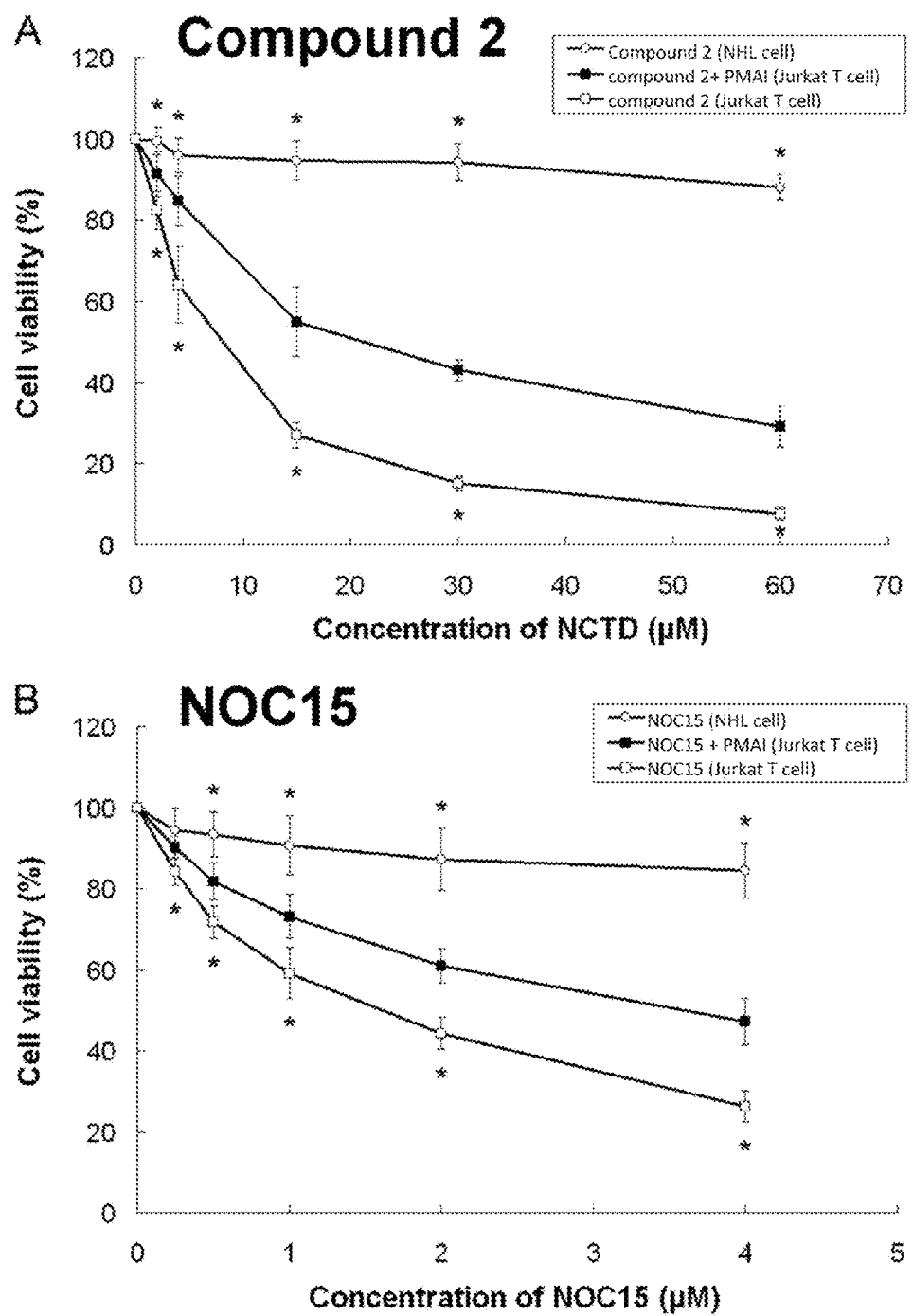
FIG. 4 are line graphs illustrating the effects of (A) compound 2 and (B) NOC15 on the viability of human leukemia cells (Jurkat T cells) and human lymphoblast cells (NHL), respectively using phorbol 12-myristate 13-acetate plus ionomycin (PMAI) activated leukemia Jurkat T cells model in accordance with one embodiment of this invention.

As depicted in FIG. 4A, compound 2 alone did not possess significant cytotoxicity to normal lymphatic cells, but was toxic to leukemia cancer Jukat T cells. Further, the percentage of viable cells increased slightly if cells were pre-treated with phorbol 12-myristate 13-acetate (PMA), an agent that is known to protect cells from apoptosis. Similar results were also observed in NOC15 treated cells (FIG. 4B). The finding confirmed that both compound 2 and NOC15 suppressed cell growth via interfering the mitogen-activated protein kinase pathway.

4.2 Cell Cycle Distribution Analysis

Cell cycle distribution was determined by flow cytometry as described in the "Materials and Methods" section. Results is depicted in FIG. 5.

It was found that only a small fraction of the control cells was in subG1 phase (FIG. 5A), whereas the percentages of cells in subG1 phase increased if they were pre-treated with NOC15 for 24 (FIG. 5B) and 48 hours (FIG. 5C), respectively. It was also noted that the percentages of leukemia cells in G2/M phase increased when treated with NOC15 for 48 hours (FIG. 5C). FIG. 5D gives the quantitative analysis of the findings in FIGS. 5A to 5C.

Example 5

Anti-Proliferative Activities of NC15 on Leukemia

5.1 Cell Viability Analysis

Figure 6:
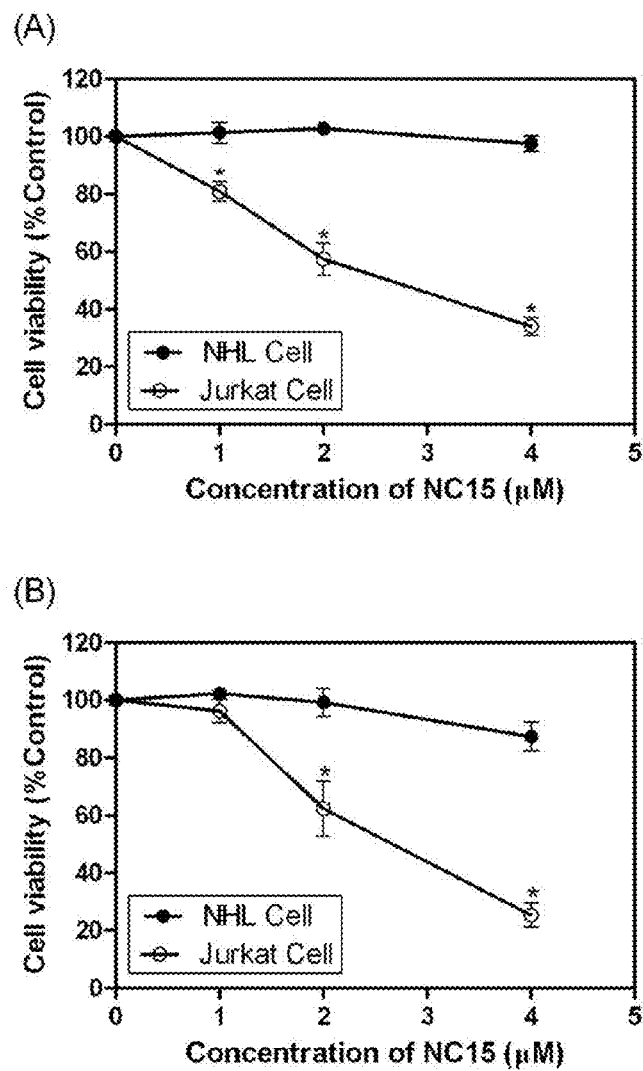
FIG. 6 are bar graphs illustrating the effect of NC15 on the viability of human leukemia cells (Jurkat T cells) and human lymphoblast cells (NHL) treated for (A) 24 and (B) 48 hours, respectively in accordance with one embodiment of this invention.

The bar graphs in FIG. 6 illustrate the cytotoxic effect of NC15 on normal human lymphoblast cells (NHL) and human leukemia Jurkat T cells. Similar to the effects of compound 2 and NOC15, NC15 alone did not possess significant cytotoxicity to normal lymphoblast cells, but was toxic to human leukemia Jurkat T cells, and the effects appeared to be dose-dependent. When cells were treated with NC15 for 24 hors, the number of viable cells decreased as the concentration of NC15 increased (FIG. 6A); similar results were observed when cells were treated for 48 hours (FIG. 6B).

5.2 Cell Cycle Analysis

In this example, Jurkat T cells were treated with or without NC15 (2.513 µM) for 24 or 48 hours before being subject to cell cycle analysis. Results are depicted in FIG. 7.

Figure 7A:
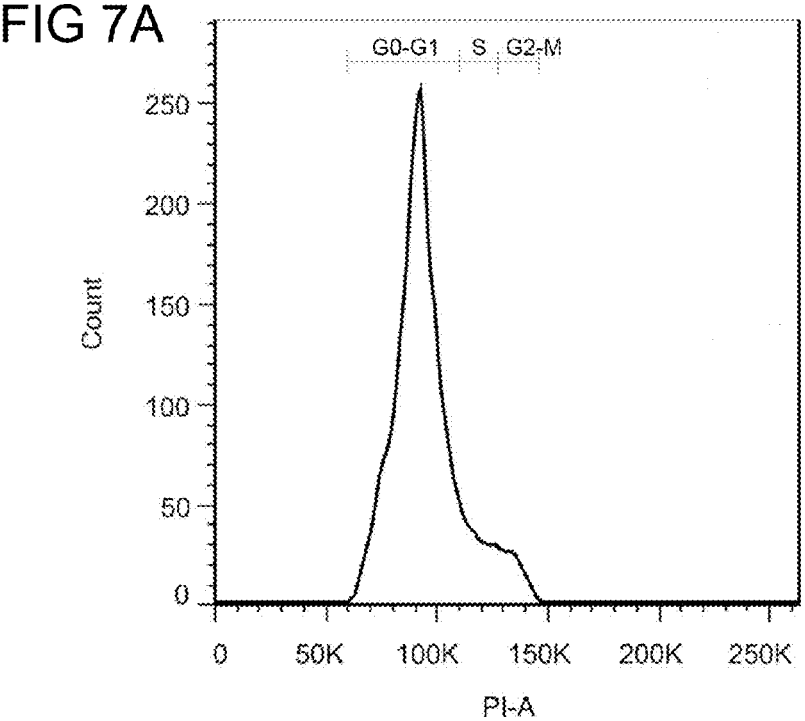
FIGS. 7A to 7C illustrate the cell cycle distribution of human leukemia cells (Jurkat T cells) treated with NC15 for (A) 0, (B) 24 and (C) 48 hours, respectively in accordance with one embodiment of this invention.
Figure 7B:
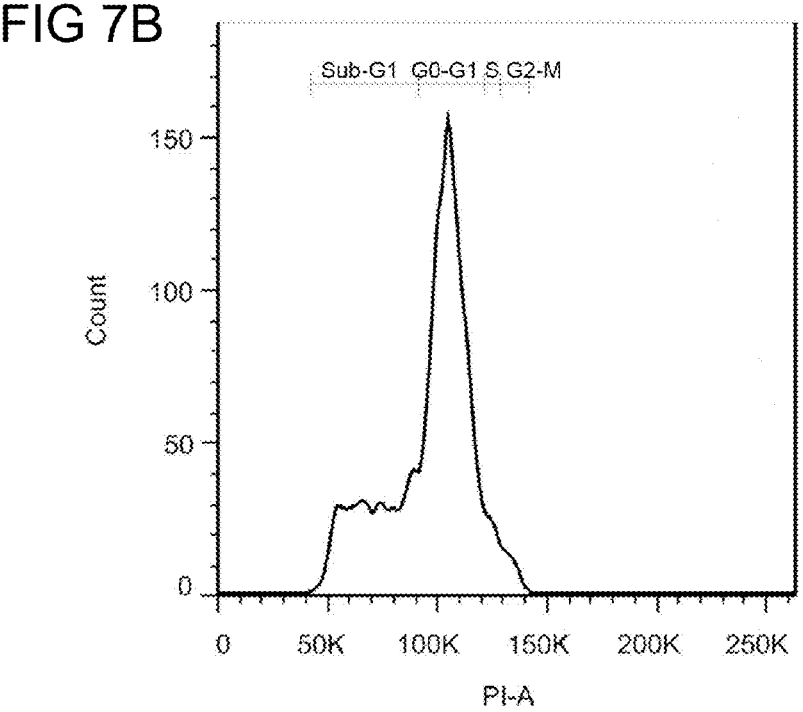
Figure 7C:
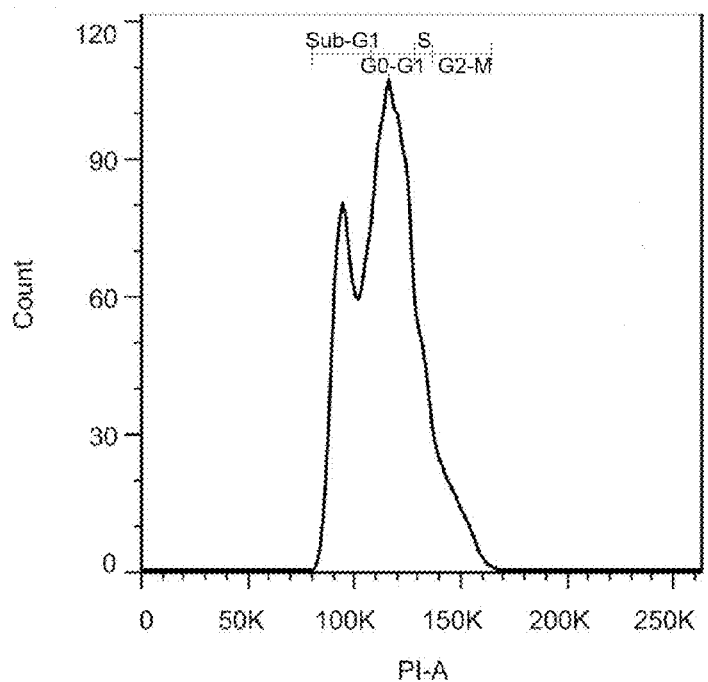
Figure 7D:
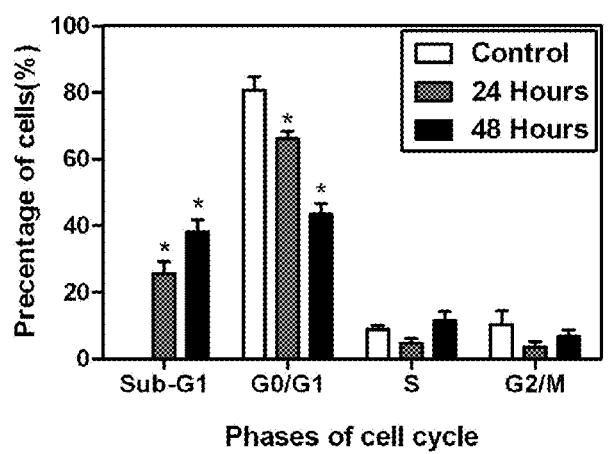
FIG. 7D illustrates the quantitated results from FIGS. 7A to 7C.
Figure 9:
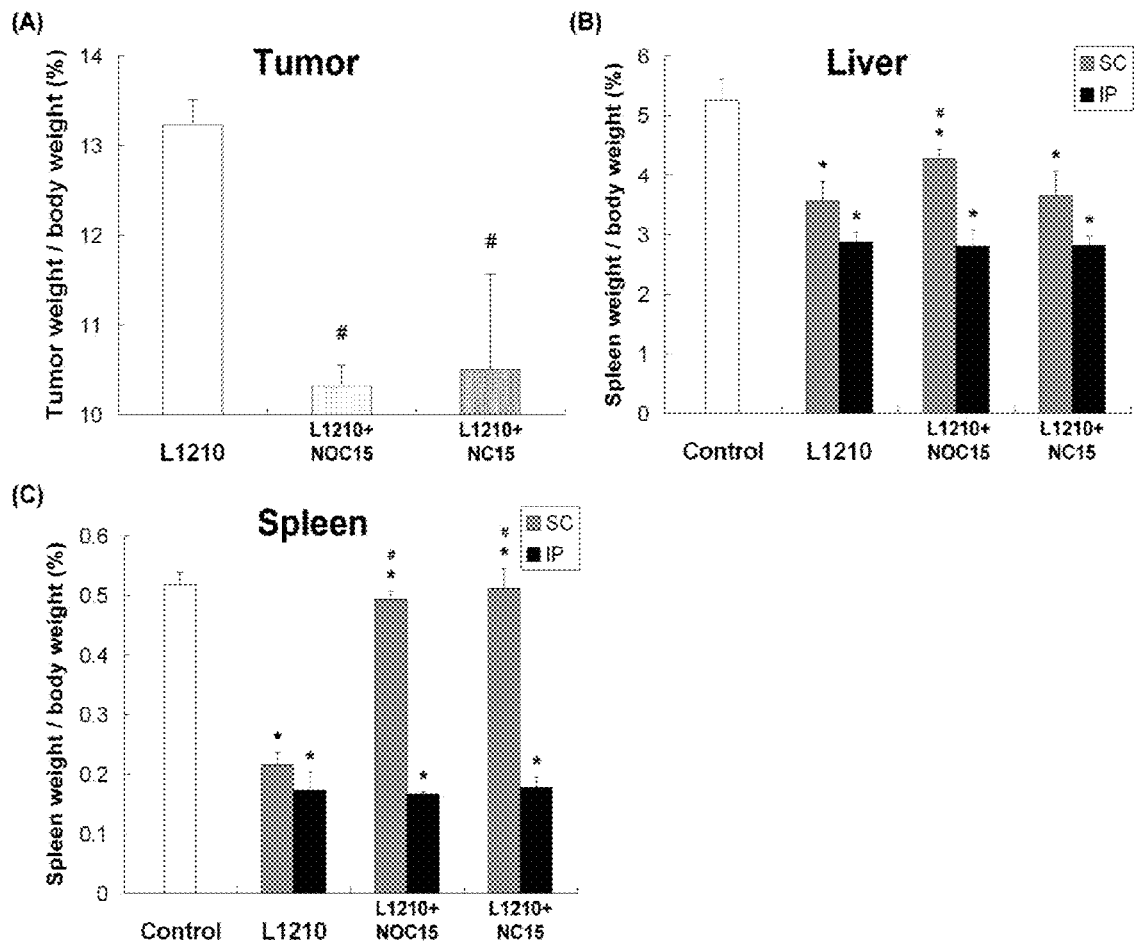
FIG. 9 illustrate the respective weight changes of (A) tumor, (B) liver and (C) spleen of animals carrying SC-injected or IP-injected leukemia cells in accordance with one embodiment of this invention.

Most of the control cells were in G0/G1 phase, after being treated with NC15 for 24 hours, the percentage of cells in the subG1 phase started to increase (FIG. 7B); by 48 hours, the population of cells in subG1 phase had reached a significant level (FIG. 7C), while the number of cells in G0/G1 phase decreased, as compared with that of the control (FIG. 7D).

5.3 NOC15 and/or NC15 Reduces Tumor Size in Animals Grafted with Human Leukemia Cancer Cell Line (L1210)

Mice were inoculated with L1210 tumor cells in accordance with the procedures described in the section of "Materials and Methods." For in vivo therapy, animals were given 18 mg/Kg NOC15 or NC15 by intra-peritoneal route, for a period of at least 7 days. Tumor size, animal body weight, respective weights of liver and spleen, as well as the white blood cell count of each animal were then measured respectively at the indicated time. Results are depicted in FIGS. 8 to 11, respectively.

Figure 10A:
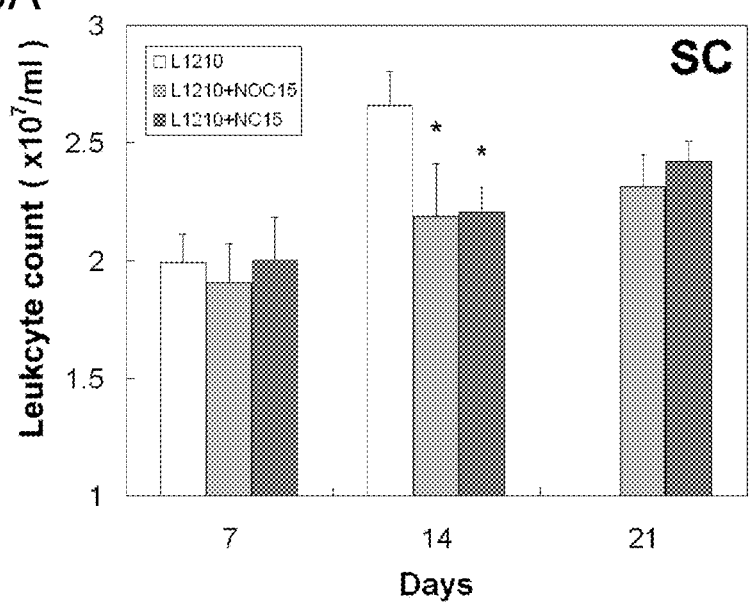
FIG. 10A illustrates the white blood cell count of animals bearing SC-injected L1210 cells treated with NOC15 or NC15 in accordance with one embodiment of this invention.
Figure 10B:
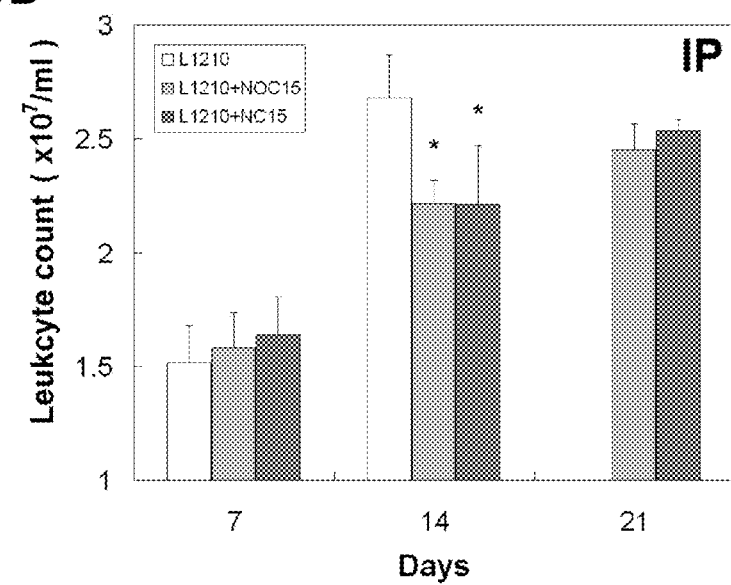
FIG. 10B illustrates the white blood cell count of animals bearing IP-injected L1210 cells treated with NOC15 or NC15 in accordance with one embodiment of this invention.

The effects of NOC15 and NC15 on the survival rate of the animals bearing (A)SC- or (B) IP-inoculated tumor are illustrated in FIG. 8. Both NOC15 and NC15 could successfully extend the life span of the animals, with about 40% increase in life span for animals bearing SC-inoculated tumors, and about 14-18% increase in animals bearing IP-inoculated tumors. Significant reduction in the weight of s.c. tumor was also observed in animals treated with NOC15 or NC15 (FIG. 9A), while the respective weights of liver and spleen in animals bearing IP-inoculated tumor improved significantly when treated with NOC15 or NC15 (FIGS. 9B and 9C). Also, significant reductions in the white blood cell (WBC) counts were observed on day 14 in the NOC15 and NC15 treated animals (FIG. 10).

Figure 11A:
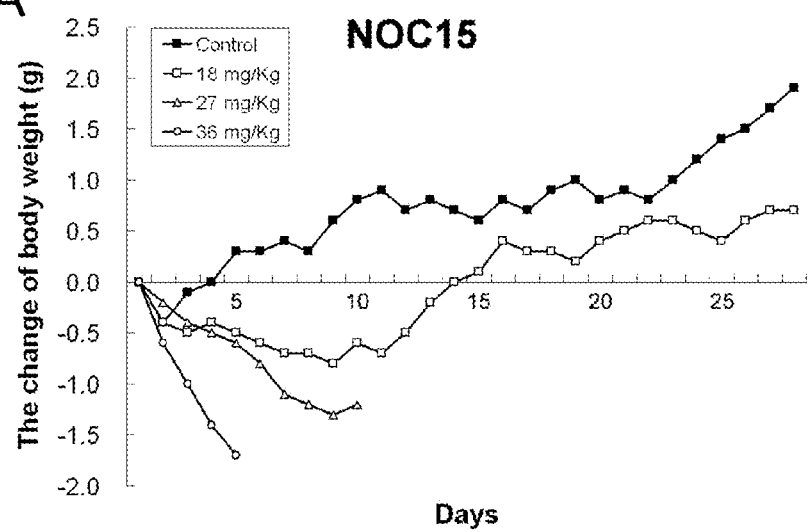
FIG. 11A illustrates the changes in body weight of animals treated with NOC15 in accordance with one embodiment of this invention.
Figure 11B:
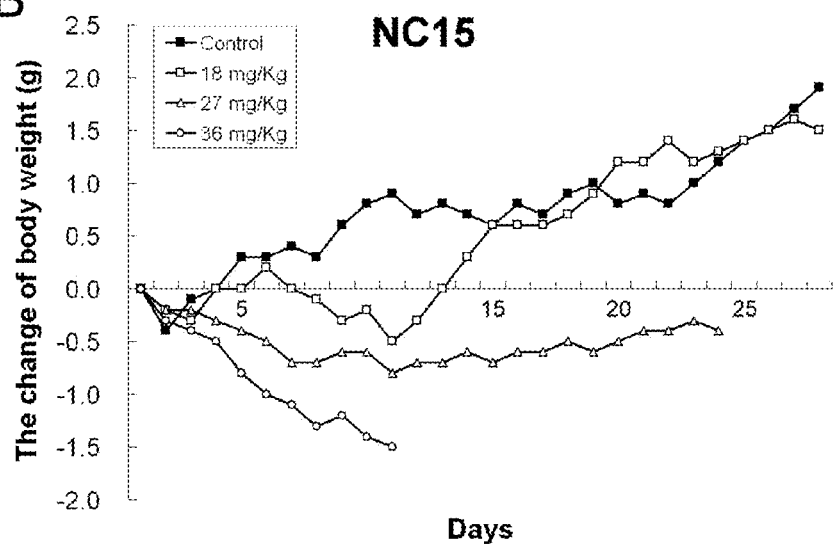
FIG. 11B illustrates the changes in body weight of animals treated with NC15 in accordance with one embodiment of this invention.

One major drawback in conventional chemotherapy is that the recipient often suffers from weight lost, which compromises the treatment effect if the recipient failed to maintain a healthy weight. Reference is now made to FIG. 11A, NOC15 given at a dose of 18 mg/Kg gradually improved the total body weight along the course of treatment, as compared with that of the control, which was a healthy normal animal without the ingestion of NOC15 or NC15; whereas NC15 given at the same dose eventually brought the animal body weight to the level same as the control (FIG. 11B). The data indicate that while NC15 is capable of suppressing tumor growth, yet it is free from the conventional "weight lost" problem commonly associated with the use of a chemotherapeutic agen; thus rendering NC15 an excellent anti-cancer drug candidate Taken together of the data presented above, we confirmed that the two novel synthesized N-substituted norcantharimide derivatives respectively possess cytotoxicity, anti-proliferative and apoptotic effects against various cancer cell lines; further, they have little or no effect toward normal lymphatic cells, thus rendering them potential candidates of the next generation anti-cancer drugs.

The foregoing description of various embodiments of the disclosure has been presented for purpose of illustration and description. It is not intended to be exhaustive or to limit the disclosure to the precise embodiments disclosed. Numerous modifications or variations are possible in light of the above teachings. The embodiments discussed were chosen and described to provide the best illustration of the principles of the disclosure and its practical application to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:
1. A compound of formula (I),

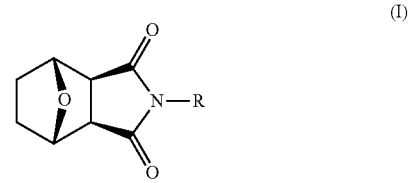

Wherein, R is farnesyl or farnesyloxy.

2. A composition for treating cancer comprising administering to a subject in need thereof an effective amount of the compound of claim 1; and a pharmaceutically acceptable excipient.

3. The composition of claim 2, wherein the cancer is selected from the group consisting of leukemia, hepatic cancer, bladder cancer, colon cancer, kidney cancer, ovarian cancer, cervical cancer, endometrial carcinoma, prostate cancer, pancreatic cancer, lung cancer, breast cancer, melanoma, and squamous cell carcinoma (SCC).

4. The composition of claim 3, wherein the cancer is leukemia.

5. The composition of claim 3, wherein the cancer is hepatic cancer.

6. A method of treating cancer comprising administering in a subject in need thereof to the subject the composition of claim 2 to suppress and/or inhibit the growth and/or metastasis of the cancer.

7. The method of claim 6, wherein in the compound of formula (I), the R is farnesyl.

8. The method of claim 6, wherein in the compound of formula (I), the R is farnesyloxy.

9. The method of claim 6, wherein the cancer is selected from the group consisting of leukemia, hepatic cancer, bladder cancer, colon cancer, kidney cancer, ovarian cancer, cervical cancer, endometrial carcinoma, prostate cancer, pancreatic cancer, lung cancer, breast cancer, melanoma, and squamous cell carcinoma (SCC).

10. The method of claim 9, wherein the cancer is leukemia.

11. The method of claim 9, wherein the cancer is hepatic cancer.

12. The method of claim 6, wherein the subject is a human.

* * * * *